US010960106B2

(12) United States Patent
Nakahara et al.

(10) Patent No.: US 10,960,106 B2
(45) Date of Patent: Mar. 30, 2021

(54) TISSUE REPAIR MATERIAL

(71) Applicant: FUJIFILM Corporation, Tokyo (JP)

(72) Inventors: Izumi Nakahara, Kanagawa (JP); Hideo Fushimi, Kanagawa (JP); Takahiro Hiratsuka, Kanagawa (JP); Ai Okamura, Kanagawa (JP); Shoji Oya, Kanagawa (JP); Hidekazu Sakai, Kanagawa (JP); Yoshitaka Oono, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/838,545

(22) Filed: Aug. 28, 2015

(65) Prior Publication Data

US 2016/0008508 A1    Jan. 14, 2016

Related U.S. Application Data

(63) Continuation of application No. PCT/JP2014/054572, filed on Feb. 25, 2014.

(30) Foreign Application Priority Data

Mar. 12, 2013  (JP) .............................. JP2013-049339

(51) Int. Cl.
| | |
|---|---|
| *A61K 38/39* | (2006.01) |
| *A61K 38/17* | (2006.01) |
| *C09H 3/00* | (2006.01) |
| *C09H 3/02* | (2006.01) |
| *A61F 13/00* | (2006.01) |
| *A61K 9/70* | (2006.01) |
| *A61K 9/14* | (2006.01) |
| *A61K 9/16* | (2006.01) |
| *A61K 9/50* | (2006.01) |
| *A61L 27/22* | (2006.01) |
| *C07K 14/78* | (2006.01) |
| *A61L 27/52* | (2006.01) |
| *A61L 31/12* | (2006.01) |
| *A61L 31/16* | (2006.01) |
| *A61L 27/54* | (2006.01) |
| *A61L 27/56* | (2006.01) |

(52) U.S. Cl.
CPC ............ *A61L 27/222* (2013.01); *A61K 38/39* (2013.01); *A61L 27/52* (2013.01); *A61L 27/54* (2013.01); *A61L 27/56* (2013.01); *A61L 31/12* (2013.01); *A61L 31/16* (2013.01); *C07K 14/78* (2013.01); *A61L 2300/412* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 4,950,483 | A | * 8/1990 | Ksander | ................. A61K 38/39 128/DIG. 8 |
| 8,987,204 | B2 | * 3/2015 | Hiratsuka | .............. C07K 14/51 424/489 |
| 2012/0165263 | A1 | 6/2012 | Hiratsuka et al. | |
| 2012/0282318 | A1 | 11/2012 | Nishida et al. | |
| 2013/0004549 | A1 | 1/2013 | Nakamura et al. | |
| 2014/0221615 | A1 | * 8/2014 | Nakada | ................... A61L 27/24 530/356 |
| 2014/0378662 | A1 | 12/2014 | Oya et al. | |

FOREIGN PATENT DOCUMENTS

| | | |
|---|---|---|
| CN | 104244999 A | 12/2014 |
| EP | 2468312 A1 | 6/2012 |
| EP | 2478923 A1 | 7/2012 |
| EP | 2543398 A1 | 1/2013 |
| EP | 2826494 A1 | 1/2015 |
| EP | 2962703 A1 | 1/2016 |
| JP | 8-196618 A | 8/1996 |
| JP | 2010-46249 A | 3/2010 |
| JP | 2011-212105 A | 10/2011 |
| WO | 2011/021706 A1 | 2/2011 |
| WO | 2011/027850 A1 | 3/2011 |
| WO | 2011/108537 A1 | 9/2011 |
| WO | WO-2013031861 A1 * | 3/2013 ............. A61L 27/24 |
| WO | 2013/137268 A1 | 9/2013 |
| WO | 2014133081 A1 | 9/2014 |

OTHER PUBLICATIONS

Merriam-Webster, "Granule", available online at https://www.merriam-webster.com/dictionary/granule, 13 pages (accessed on Feb. 14, 2017).*
Esposito et al., Biomaterials 17:2009-2020 (2006).*
Communication dated Apr. 14, 2016 from the State Intellectual Property Office of the P.R.C. issued in corresponding Application No. 201480011883.4.
Communication dated Mar. 1, 2016, from the European Patent Office in counterpart European Application No. 14765519.5.
Communication dated Feb. 2, 2016, from the Japanese Patent Office in counterpart application No. 2015-505378.
Office Action dated Dec. 12, 2017 in counterpart Chinese Application No. 201480011883.4.

(Continued)

*Primary Examiner* — Thea D' Ambrosio
(74) *Attorney, Agent, or Firm* — Sughrue Mion, PLLC

(57) ABSTRACT

A tissue repair material includes gelatin granules, and the tissue repair material exhibits a water absorptivity of 800% by mass or more, and a residual ratio of 60% by mass or less after three hours of decomposition treatment using 1 mol/L hydrochloric acid. A block-shaped tissue repair material includes gelatin, and the block-shaped tissue repair material exhibits a water absorptivity of 800% by mass or more, and a residual ratio of 60% by mass or less after three hours of decomposition treatment using 1 mol/L hydrochloric acid.

10 Claims, No Drawings

Specification includes a Sequence Listing.

(56) References Cited

OTHER PUBLICATIONS

International Search Report for PCT/JP2014/054572 dated May 20, 2014 [PCT/ISA/210].

Written Opinion for PCT/JP2014/054572 dated May 20, 2014 [PCT/ISA/237].

* cited by examiner

TISSUE REPAIR MATERIAL

CROSS-REFERENCE TO RELATED APPLICATIONS

This application is a continuation application of International Application No. PCT/JP2014/054572, filed Feb. 25, 2014, the disclosure of which is incorporated herein by reference in its entirety. Further, this application claims priority from Japanese Patent Application No. 2013-049339, filed Mar. 12, 2013, the disclosure of which is incorporated herein by reference in its entirety.

TECHNICAL FIELD

The present invention relates to a tissue repair material.

BACKGROUND ART

Progress is currently being made in the implementation of regenerative medicine to regenerate biological tissues or organs with impaired function or lost function. Regenerative medicine is new medical technology that uses the three factors of cells, scaffolding, and growth factors on a biological tissue that has lost the ability to recover by its own natural healing abilities, and reestablishes a morphology and a function similar to those of the original tissue.

Bone regeneration in the fields of orthopedics and dentistry is a field within regenerative medicine that is attracting considerable attention. In bone diseases affecting the feet and hips, bone defect caused by the disease may result in loss of ability to walk. In the case of a bone disease in the periodontal tissue, the bone disease makes meal ingestion difficult. Bone diseases therefore cause a significant drop in the QOL.

Collagen or gelatin, which has high biocompatibility, is employed as a substrate in the field of regenerative medicine.

For example, International Publication (WO) No. 2011/027850 discloses a bone regeneration agent and a bone prosthetic formulation that include a recombinant gelatin, and in which the prosthetic support is capable of promoting bone regeneration by itself.

Japanese Patent Application Laid-Open (JP-A) No. H08-196618 discloses a cell penetrable collagen formulation formed from a sponge-like collagen matrix having numerous pores. JP-A Nos. 2001-212105 and 2010-046249 disclose a bone prosthetic material in which bio-ceramic granules are used as a granular bone prosthetic material.

SUMMARY OF INVENTION

However, when a block-shaped sponge such as the cell penetrable collagen formulation described in JP-A No. H08-196618 is used, a high degree of communication between sponge pores is required to ensure cell penetrability to the block interior, and this makes it difficult to increase the overall elasticity of the block. When collagen is used as the material, it is difficult to prepare a collagen solution having high concentrations, and producing a sponge-like material having high elasticity is difficult. Therefore, in a case in which such a material is used as a prosthetic material, and in which the bone-missing area is located at a site that is normally under pressure, the volume of the bone-missing area may not be maintained. In the case of bone prosthetic agents made from bioceramic granules, there are cases where the bone prosthetic agents remain in the body for a long period of time, and do not allow substitution by regenerated bone. Thus, each of the technologies described above still has room for improvement from the viewpoint of obtaining a tissue repair material that promotes regeneration of a tissue such as bone.

The invention addresses provision of a tissue repair material having high ability to regenerate a tissue such as bone.

The invention includes the following aspects:

[1] A tissue repair material including gelatin granules, the tissue repair material exhibiting a water absorptivity of 800% by mass or more, and a residual ratio of 60% by mass or less after three hours of decomposition treatment using 1 mol/L hydrochloric acid.

[2] The tissue repair material according to [1], wherein the gelatin granules include a granular gelatin that passes through a sieve having openings of 1400 μm.

[3] The tissue repair material according to [1] or [2], wherein the gelatin granules include a crosslinked product of gelatin.

[4] The tissue repair material according to any one of [1] to [3], wherein the gelatin granules include a thermally crosslinked product of gelatin.

[5] The tissue repair material according to any one of [1] to [4], wherein the tissue repair material is granular.

[6] The tissue repair material according to any one of [1] to [5], wherein the tissue repair material is a substrate for bone regeneration.

[7] A block-shaped tissue repair material including gelatin, the block-shaped tissue repair material exhibiting a water absorptivity of 800% by mass or more, and a residual ratio of 60% by mass or less after three hours of decomposition treatment using 1 mol/L hydrochloric acid.

According to the invention, a tissue repair material can be provided that exhibits high ability to regenerate a tissue such as bone.

DESCRIPTION OF EMBODIMENTS

In the present specification, the word "process" does not only refer to an independent process, and a given process that cannot be clearly distinguished from another process is also encompassed by the word as long as the specified effects of the given process are obtained.

Numerical ranges indicated by "to" in the present specification indicate ranges in which the numerical values before and after the "to" are included as the respective lower value and upper value of the range.

In the invention, when plural substances exist that correspond to a given component in a composition, the content of the given component in the composition refers to the total content of the plural substances present in the composition, unless otherwise stated.

In the invention, amino acid sequences of polypeptides are sometimes denoted using single letter symbols (for example, "G" for a glycine residue) or three letter symbols (for example, "Gly" in the case of a glycine residue), which are known in the relevant technical field.

In the invention, the use of "%" in relation to amino acid sequences of polypeptides is based on the number of amino acid (or imino acid) residues unless otherwise stated.

In the invention, the use of "identity" in relation to the amino acid sequences of two polypeptides being compared refers to a value calculated by the equation below. Comparison (alignment) of plural polypeptides is performed according to ordinary methods such that the number of matching amino acid residues is maximized.

$$\text{Identity (\%)} = \{(\text{number of identical amino acids})/(\text{alignment length})\} \times 100$$

Explanation regarding the invention follows.

The tissue repair material according to the invention includes gelatin granules and exhibits a water absorptivity of 800% by mass or more, and a residual ratio of 60% by mass or less after three hours of decomposition treatment using 1 mol/L hydrochloric acid.

The value of the residual ratio specified above indicates a decomposition ratio of 40% by mass or more after three hours of decomposition treatment using 1 mol/L hydrochloric acid.

Hereafter, the residual ratio as defined above is also referred to as a "residual ratio in the presence of acid".

The tissue repair material according to the invention is configured to exhibit an excellent tissue regeneration ability by including gelatin granules and being made to exhibit the water absorptivity and the residual ratio in the presence of acid as specified above. More specifically, the following mechanism is conceivable:

the tissue repair material is capable of holding blood clots at a tissue defect area due to having the specified water absorptivity, and the strength of the tissue repair material is ensured for a desired period of time due to having the specified residual ratio in the presence of acid, namely, the specified decomposition ratio, whereby the tissue repair material is able to act as a location to be substituted by regenerated bone while maintaining the volume of the defect area; and, as a result, placing the tissue repair material in the defect area enables regeneration of a tissue such as bone to proceed in a favorable manner. However, the invention is not restricted by such reasoning.

The tissue repair material according to the invention may include other components, if necessary.

In the invention, "gelatin granules" refers to a collection of gelatin granules unless otherwise stated.

After performing a process to prepare the granular gelatin, the gelatin granules included in the tissue repair material according to the invention may be independent from one another or may be adhered to one another; however, the gelatin granules are preferably independent from one another.

The tissue repair material according to the invention, which includes gelatin granules, is preferably granular. "The tissue repair material is granular" denotes that the granules that are independent from one another or adhered to one another are in a state in which the granules can pass through a sieve having openings of 4 mm.

"Block shaped" in a blocked shaped tissue repair material according to the invention denotes that the tissue repair material has at least one axis with a length of 5 mm or more. If there is one axis with a length of 5 mm or more, any other axes may be 5 mm or less, to give a shape such as a rod shape or a sheet shape.

"Tissue repair material" in the invention refers to a material that, as a result of being implanted in a biological organism, contributes to formation of a tissue at the implantation site, and the tissue repair material may include a cell or may be free of cells. Moreover, the tissue repair material may include a component that stimulates a response in the biological organism, such as growth factors or drugs, or may be free of components that stimulate a response in the biological organism such as growth factors or drugs. Moreover, a mixture or composite with an inorganic material such as hydroxyapatite may be produced and applied. However, when measuring the water absorptivity and the residual ratio in the presence of acid in the invention, these are measured with respect to a mass that excludes any such cells or inorganic materials.

In the invention, "tissue repair material" does not necessarily refer to a material that contributes to formation of an ordinary tissue that would ordinarily be present at the implantation site; the scope of "tissue repair material" also encompasses materials that promote formation of an abnormal tissue such as a scar tissue.

Gelatin

The gelatin may be a natural form of gelatin, or may be a mutant form or recombinant form of gelatin that differs from the natural form by at least one amino acid residue. Natural form of gelatin refers to a gelatin obtained from a naturally occurring gelatin as a raw material, or a polypeptide having the same amino acid sequence as that of a gelatin obtained from a naturally occurring collagen as a raw material. In the present specification, mutant forms of gelatin or recombinant forms of gelatin are both referred to as recombinant gelatin, unless otherwise stated. Natural forms of gelatin and recombinant forms thereof include those derived from animals such as fish and mammals, and natural gelatins of mammalian animals and recombinant gelatins thereof are preferable. Examples of mammalian animals include humans, horses, pigs, mice, and rats, and humans and pigs are more preferable. The natural form of gelatin is preferably derived from a pig or human, and the recombinant gelatin is preferably a human-derived recombinant gelatin.

Gelatin refers to a polypeptide that consecutively includes 6 or more amino acid sequence units each represented by Gly-X—Y, and one or more amino acid residues other than the amino acid sequence represented by Gly-X—Y may be included in the polypeptide. Here, Gly in Gly-X—Y represents a glycine residue, and X and Y each represent any amino acid residue other than glycine. The amino acid sequence represented by Gly-X—Y is a sequence corresponding to an amino acid sequence derived from a partial amino acid sequence of collagen, and repetition of this sequence represents a characteristic sequence for the collagen.

The plural Gly-X—Y units in a single gelatin molecule may be identical to one another, or may be different from one another. With respect to the X and Y in the Gly-X—Y sequence, X's and Y's in respective repeating units are mutually independent, and X and Y may be identical to each other or different from each other. The amino acid residues represented by X's and Y's preferably include many imino acid residues, namely, proline residues or oxyproline residues. The content ratio of imino acid residues, such as those described above, in a single gelatin molecule is preferably from 10% to 45% of the gelatin molecule. The content ratio of Gly-X—Y in a single gelatin molecule is preferably 80% or more, more preferably 95% or more, and most preferably 99% or more, with respect to the total amino acid residues.

The gelatin is preferably a recombinant gelatin obtained by introducing an amino acid sequence or base sequence into an appropriate host using an ordinary method and expressing the same, the amino acid sequence or base sequence being obtainable by modifying one or more amino acid or base residues from an amino acid sequence or base sequence of a gene coding for a collagen consecutively including 6 or more amino acid sequence units each represented by Gly-X—Y. Employing such a recombinant gelatin increases bone regeneration ability, and enables various characteristics to be expressed, compared to a case in which natural gelatin is employed. Employing such a recombinant gelatin has an advantage of, for example, enabling negative consequences such as a rejection response by the biological organism to be avoided.

Examples of recombinant gelatin that are particularly preferably employed include those described in EP 1014176A2, U.S. Pat. No. 6,992,172B1, WO2004/85473A2, WO2008/103041A1, Japanese National-Phase Patent Publication (JP-A) Nos. 2010-519293, 2010-519252, 2010-518833, and 2010-519251, WO2010/128672A1, and WO2010/147109A1.

The recombinant gelatin preferably has a molecular weight of from 2 kDa to 100 kDa, more preferably from 5 kDa to 90 kDa, and more preferably from 10 kDa to 90 kDa.

From the viewpoint of biocompatibility, the recombinant gelatin preferably further includes a cell adhesion signal, and more preferably includes two or more cell adhesion signals in a single molecule. Examples of such cell adhesion signals include an RGD sequence, an LDV sequence, an REDV sequence (SEQ ID NO: 3), a YIGSR sequence (SEQ ID NO: 4), a PDSGR sequence (SEQ ID NO: 5), an RYVVLPR sequence (SEQ ID NO: 6), an LGTIPG sequence (SEQ ID NO: 7), an RNIAEIIKDI sequence (SEQ ID NO: 8), an IKAVAV sequence (SEQ ID NO: 9), an LRE sequence, a DGEA sequence (SEQ ID NO: 10), and a HAV sequence. Preferable examples include an RGD sequence, a YIGSR sequence (SEQ ID NO: 4), a PDSGR sequence (SEQ ID NO: 5), an LGTIPG sequence (SEQ ID NO: 7), an IKAVAV sequence (SEQ ID NO: 9), and a HAV sequence. An RDG sequence is particularly preferable. Among RDG sequences, an ERGD sequence (SEQ ID NO: 11) is more preferable.

The placement of RDG sequence units in the recombinant gelatin is preferably such that there are from 0 to 100 amino acid residues, and more preferably from 25 to 60 amino acid residues, between each RGD sequence unit. RDG sequence units are preferably positioned non-uniformly, within the above-described range of the number of amino acid residues is satisfied.

The ratio of RGD sequence units with respect to the total number of amino acid residues in the recombinant gelatin (the total number of amino acid residues of RGD sequence units/the total number of amino acid residues×100) is preferably at least 1.2%, and when the recombinant gelatin includes 250 amino acid residues or more, it is preferable that there is at least one RGD sequence unit included in each stretch of 250 amino acid residues.

The recombinant gelatin preferably includes at least two RGD sequence units, more preferably includes at least 3 RGD sequence units, and still more preferably includes at least 4 RGD sequence units, for every 250 amino acid residues.

The sequence of the recombinant gelatin preferably has any of the following features: (1) includes no serine residues or threonine residues, (2) includes no serine residues, threonine residues, asparagine residues, tyrosine residues, or cysteine residues, or (3) includes no amino acid sequences represented by Asp-Arg-Gly-Asp (SEQ ID NO: 12). The recombinant gelatin may have one of these preferable sequence features (1) to (3), or may have a combination of two or more of these features.

The recombinant gelatin may be partially hydrolyzed.

The recombinant gelatin preferably includes an amino acid sequence of A-[(Gly-X—Y)$_n$]$_m$—B. Herein, A represents one freely selected amino acid residue or two or more freely selected amino acid residues, B represents one freely selected amino acid residue or two or more freely selected amino acid residues, Gly represents glycine, X, n in number, each independently represents a freely selected amino acid residue, and Y, n in number, each independently represents a freely selected amino acid residue. Further, m represents an integer of from 2 to 10, and preferably represents an integer of from 3 to 5. Moreover, n represents an integer of from 3 to 100, preferably represents an integer of from 15 to 70, and more preferably represents an integer of from 50 to 60. The m units of Gly-X—Y may all be identical to one other, or some, but not all, of them may be identical to one another, or they may be different from one another.

The recombinant gelatin more preferably includes an amino acid sequence of Gly-Ala-Pro-[(Gly-X—Y)$_{63}$]$_3$-Gly (SEQ ID NO: 2). Here, X (=Xaa), 63 in number, each independently represents a freely selected amino acid residue, and Y (=Xaa), 63 in number, each independently represents a freely selected amino acid residue. The 63 units of Gly-X—Y may all be identical to one other, or some, but not all, of them may be identical to one another, or they may be different from one another.

With respect to the repeating units of the recombinant gelatin, it is preferable that a portion of an amino acid sequence of a collagen that exists in nature serves as a unit, and that the recombinant gelatin is formed by bonding two or more of this unit. Preferable examples of the collagen that exists in nature referred to include type I, type II, type III, type IV, and type V collagens, and the collagen is more preferably Type I, type II, or type III collagen. Preferable examples of collagen sources include humans, horses, pigs, mice, and rats, and a human is more preferable as a collagen source.

The isoelectric point of the recombinant gelatin is preferably from 5 to 10, more preferably from 6 to 10, and still more preferably from 7 to 9.5.

Preferable examples of features that the recombinant gelatin may have include the following: (1) carbamoyl groups being unhydrolyzed, (2) procollagen not being included, (3) telopeptides not being included, and (4) the recombinant gelating being a substantially pure collagen-like material prepared using a nucleic acid coding for a natural collagen. The recombinant gelatin may have one of these preferable features (1) to (4), or may have a combination of two or more of these features.

From the viewpoint of the level of tissue repair ability, the recombinant gelatin is preferably any of (A) to (C) below.

(A) A polypeptide represented by SEQ ID NO: 1 below.

```
                                              (SEQ ID NO: 1)
GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)₃G
```

(B) A polypeptide that includes a partial sequence that has a sequence identity of 80% or higher to a partial amino acid sequence formed from the 4$^{th}$ to the 192$^{nd}$ amino acid residues in the amino acid sequence (A), and that has the ability to regenerate a tissue.

(C) A polypeptide that is formed from an amino acid sequence obtainable by modifying the amino acid sequence of (A) by deletion, substitution or addition of one or several amino acid residues, and that has the ability to regenerate a tissue.

From the viewpoint of tissue regeneration ability of the recombinant gelatin, the sequence identity for (B) is preferably 90% or higher, and is more preferably 95% or higher.

The partial amino acid sequence of (B) is a partial amino acid sequence corresponding to the repeating unit of the sequence represented by SEQ ID NO: 1. When the polypeptide of (B) includes plural portions having a partial amino acid sequence corresponding to the repeating unit, the polypeptide may include one, or preferably two or more, repeating units each having a sequence identity of 80% or more to the repeating unit of the sequence represented by SEQ ID NO: 1.

The polypeptide defined by (B) preferably includes one or more partial sequences each having a sequence identity of 80% or higher to the partial amino acid sequence corresponding to the repeating unit of the sequence represented by SEQ ID NO: 1, in an overall number of amino acid residues of 80% or more with respect to the total number of amino acid residues.

The length of the polypeptide defined by (B) may be set to a number of amino acid residues of from 151 to 2260, and the number of amino acid residues is preferably 193 or more from the viewpoint of degradability after crosslinking, is preferably 944 or less from the viewpoint of stability, and is more preferably from 380 to 756 amino acid residues.

In the polypeptide defined by (C), the number of amino acid residues that are removed, substituted, or added may be one residue or several residues. The number of amino acid residues that are removed, substituted, or added varies depending on the total number of amino acid residues of the recombinant gelatin, and is, for example, from 2 to 15, preferably from 2 to 5.

The recombinant gelatin can be produced by genetic recombination techniques known to those skill in the art, and, for example, may be produced according to the methods described in EP 1014176A2, U.S. Pat. No. 6,992,172B1, and WO Nos. 2004/85473A2 and 2008/103041A1.

The evaluation of the tissue regeneration ability of the polypeptides defined by (B) and (C) may be performed using a tissue repair material obtained using the recombinant gelatin. The evaluation method varies with the target tissue.

For example, bone regeneration ability may be evaluated by: producing a bone loss area of a specific size in the parietal bone of a rat, filling the tissue repair material into the bone loss area and then suturing the skin, measuring the amount of bone four weeks after the surgical procedure using microCT, and evaluating the bone regeneration ability as the ratio of the volume of regenerated bone to the volume of the bone loss area.

The gelatin granules preferably include a crosslinked product of gelatin from the viewpoint of being able to maintain the volume of the preparation layer provided in a bone loss area for the required time period. Examples of the crosslinked product include a chemically-crosslinked product formed using a crosslinking agent, and a thermally-crosslinked product, and a thermally-crosslinked product is preferable from the viewpoint of not using a crosslinking agent. Inclusion of the crosslinked product in the gelatin granules can be confirmed based on a state in which the gelatin granules do not dissolve in warm water. Here, "do not dissolve in warm water" denotes that solubility in water at 37° C. is 50% by mass or lower.

In the present specification, the term "preparation layer" refers to a layer formed by placing the tissue repair material in a specific space, and, similarly to the technical term "particle bed", the preparation layer refers to an overall structure including both the plural particles of the preparation filling a specific space, and gaps between the particles of the preparation.

Gelatin Granules

The gelatin granules included in the tissue repair material are particles that pass through a sieve having openings of 4 mm. From the viewpoint of cell invasion, the gelatin granules are preferably particles that pass through a sieve having openings of 1400 µm, are more preferably particles that pass through a sieve having openings of 1000 µm, and are still more preferably particles that pass through a sieve having openings of 710 µm. From the viewpoint of maintaining elasticity of the preparation layer, the gelatin granules are preferably particles that remain in a sieve having openings of 75 µm after sieving, and are more preferably particles that remain in a sieve having openings of 300 µm after sieving.

The sieving of gelatin granules is performed using an assay sieve according to ISO 3310, and the sieving method is based on the sieving method described in the Japanese Pharmacopoeia 16th edition, section 3.04, Second Method. Namely, five minutes of shaking is performed plural times with intervals therebetween, and the sieving is completed when the mass of particles present in the sieve after shaking become 5% or less of the mass of particles placed on the sieve before shaking. In the invention, the term "pass through" denotes that the mass of particles present in the sieve at the completion of sieving is 10% or less of the total mass of particles before sieving, and the term "remain" denotes that the mass of particles remaining in the sieve at the completion of sieving is 95% or more of the total mass of particles before sieving.

When the gelatin included in the tissue repair material is granular rather than block-shaped (clumped) body or the like, a high density gelatin solution can be prepared and used, and cell invasion to up to the center of the loss area can be ensured even when the substrate has a higher density. Due to this configuration, when the tissue repair material is placed at the loss area to form a preparation layer, excellent tissue regeneration ability, particularly, bone regeneration ability, can be exhibited without a decrease in the volume of the preparation layer even under pressure.

From the viewpoint of tissue formation ability, the individual gelatin granules of the tissue repair material are preferably porous bodies having spaces. From the viewpoint of cell invasion, there are preferably spaces between the particles in the preparation layer formed by placing the gelatin granules in the loss area, and the void ratio of the preparation layer overall is preferably from 70% to 96.5%, and is more preferably from 80% to 90%. The void ratio is obtained as a void ratio ($P=(1-\rho t/\rho c)\times 100(\%)$) calculated from a tapped density ($\rho t$) and a true solid density ($\rho c$) described below. The tapped density ($\rho t$) is obtained using the method described below. The true solid density ($\rho c$) is obtained according to the pycnometer method using a Hubbard-type pycnometer.

The individual gelatin granules in the tissue repair material may have communicating holes. The presence of communicating holes allows spaces to be continuous from the outside of the tissue repair material to deep inside the tissue repair material, whereby cells in contact with the outside of the tissue repair material can disperse or diffuse into the interior of the tissue repair material. For the above functionality to be exhibited, the hole diameter of the communicating holes is preferably from 10 µm to 2500 µm, more preferably from 50 µm to 2500 µm, and particularly preferably from 100 µm to 1000 µm.

Tapped Density

The tapped density is a value representing the extent to which granules can be densely packed into a given volume. The smaller this value is, the more complex the structure of the granules tends to be, the wider the distribution of granule sizes tends to be, and the sparser the filling tends to be. The shape of the granules obtained after pulverization varies due to differences in the gelatin structure created during freezing, and various sizes of granules are obtained by pulverization. In consideration of these, the tapped density, as defined in the present specification, is preferably from 10 mg/cm$^3$ to 500 mg/cm$^3$, is more preferably from 30 mg/cm$^3$ to 450 mg/cm$^3$, is still more preferably from 50 mg/cm$^3$ to 420 mg/cm$^3$, and is even more preferably from 140 mg/cm$^3$ to 280 mg/cm$^3$. A tapped density of 10 mg/cm$^3$ or more tends to facilitate an increase in the elasticity of the preparation layer, and to facilitate maintenance of the volume of the loss area. A tapped density of 500 mg/cm$^3$ or less tends to facilitate suppression of a decrease in invasion of cells, and to facilitate obtainment of sufficient healing effects.

The method employed for measuring the tapped density is as follows. A cylindrical vessel (referred to as a cap hereafter) of 6 mm diameter and 21.8 mm length (volume 0.616 cm$^2$) is prepared for the purpose of the measurement. First, the mass (wt) of the cap alone is measured. Then, a funnel is connected to the cap, and granules are poured into the cap through the funnel such that the granules are collected in the cap. After a sufficient amount of granules are pored, the cap portion is hit against a hard object such as a desk 200 times, the funnel is removed, and any granules above the edge of the cap are leveled off with a spatula. The mass (wg) is measured in a state in which the granules are level full in the cap. The mass of the granules alone is computed from the difference from the mass of the cap alone, and the tapped density is obtained by dividing by the volume of the cap.

Tapped density: $\rho t=(wg-wt)/0.616$

Water Absorptivity

The tissue repair material exhibited a water absorptivity of 800% or higher by mass. High tissue regeneration ability is not obtainable if the water absorptivity is less than 800%. From the viewpoint of holding blood clots during tissue recovery, the water absorptivity of the tissue repair material is preferably 900% or more, is more preferably 1200% or more, and is still more preferably 1400% or more. Although not particularly limited, the maximum value of the water absorptivity of the tissue repair material is preferably 9900% or less, is more preferably 5000% or less, and is still more preferably 3000% or less. When only gelatin granules are included in the tissue repair material, the water absorptivity of the tissue repair material is the water absorptivity of the gelatin granules.

"Water absorptivity" of the tissue repair material in the invention refers to a physical characteristic measured as described below. Measurement is performed in a room with a relative humidity from 30% to 60%, preferably 40%, within a temperature range of from 21° C. to 26° C., preferably at 25° C.

The mass (A) is measured of a mesh bag made from nylon for measuring (referred to below as a mesh bag) having a size of 3 cm×3 cm and a thickness of 106 μm and having a mesh with 150 strands per 2.54 cm, a strand diameter of 6 μm, an opening equivalent to 108 μm, and an opening area of 41%. In the case of a granular tissue repair material, 15.0 (±1.0) mg thereof is weighed out in the form for placement in the tissue defect area, without processing. In the case of a block-shaped tissue repair material, a rectangular parallelepiped sample thereof having a size of approximately 1.5 mm×approximately 2 mm×approximately 12 mm is prepared, the mass (B) thereof is measured, and the sample is inserted into the mesh bag for measuring. The mesh bag for measuring is employed in an empty state without inserting tissue repair material as a blank mesh bag, and the mass (C) thereof is measured. Clips are placed on the upper faces of both of the mesh bags, and the mesh bags are suspended in 100 ml beakers containing 80 ml of ultrapure water. Both mesh bags are retained in the position at which all of the tissue repair material in the bag would be soaked in water, and are left for two hours or longer. After two or more hours have elapsed, the water in the beakers is discarded and both mesh bags are taken out, both are hung at the same angle of inclination and left to stand for 10 minutes to drain excess water. Then, the mass (D) of the blank mesh bag, and the mass (E) of the mesh bag containing the tissue repair material are measured, and the water absorptivity is calculated using Equation (1) and Equation (2) below.

Blank water absorptivity $(F)=D/C$     (1)

Water absorptivity $=(E-A \times F)/B \times 100(\%)$     (2)

The water absorptivity of the tissue repair material varies depending on the components included in the tissue repair material, particularly, the type of gelatin granules and the form of individual gelatin granules. The water absorptivity of the tissue repair material may, for example, be regulated based on the temperature, processing time or the like in the freezing process or the crosslinking process in the method of manufacturing a tissue repair material described below. Generally, the water absorptivity tends to increase as the temperature of the freezing process is increased, the temperature of the crosslinking process is lowered, or the crosslinking time is shortened.

Acid Degradability

The tissue repair material exhibits a residual ratio of 60% by mass or less after three hours of decomposition treatment using 1 mol/L (liter) hydrochloric acid. The tissue regeneration ability is not sufficient when the residual ratio is higher than 60% by mass after three hours decomposition treatment using 1 mol/L hydrochloric acid. From the viewpoints of maintaining the volume of the preparation layer at the defect area, and substitution with a regenerating tissue, the residual ratio of the tissue repair material in the presence of acid is preferably 5% by mass or more, is more preferably 20% by mass or more, and is still more preferably 40% by mass or more. When the tissue repair material includes only gelatin granules, the residual ratio of the tissue repair material in the presence of acid is the residual ratio of the gelatin granules in the presence of acid.

The "residual ratio in the presence of acid" of the tissue repair material according to the invention refers to a physical characteristic value measured as described below. The mass (A) of a microtube for measuring (trade name MINI SUPERTUBE, manufactured by Ibis, capacity 2 ml, referred to as a tube hereafter) is measured. In the case of a granular repair material, 5.0 (±0.2) mg thereof is weighed out in the form for placement in the tissue defect area, without processing. In the case of a block-shaped repair material, a solid cylindrical sample having a size of 6 mm diameter×approximately 1 mm thickness is prepared, the mass thereof (B) is measured, and the sample is inserted into the tube for measuring. 1.0 ml of 1 mol/L HCl is then added into the tube containing the tissue repair material, and shaken in a thermostatic shaker (a HB-80 (manufactured by Taitec Corporation) with a see-saw movement at 60 reciprocal movements per minute) at 37° C. for three hours. After the stipulated time, the tube is stood on ice to stop reactions, and then centrifuged at 10,000×g for one minute in a centrifuge pre-set to 4° C. Precipitation of the tissue repair material is confirmed, the supernatant is removed by suction, 1 ml of ultrapure water, pre-cooled on ice, is added thereto, and centrifuging is performed again under the same conditions as above. The supernatant is removed by suction, ultrapure water is again added thereto, and centrifuging is performed again under the same conditions as above. The supernatant is then removed by suction, then freeze-drying is performed. After the tube is taken out from the freeze-drying apparatus, the cap of the tube is quickly closed in order to prevent the tissue repair material from absorbing moisture in the air. The mass (C) of the tube including the content thereof is measured, and the residual ratio in the presence of acid is computed using calculation Equation (3) below.

$$\text{Residual ratio in the presence of acid} = (C-A)/B \times 100 (\%) \quad (3)$$

The residual ratio of the tissue repair material in the presence of acid varies depending on the components included in the tissue repair material, particularly, the type and form of the gelatin granules. The residual ratio of the tissue repair material in the presence of acid can be regulated, for example, based on the temperature, processing time or the like in the crosslinking process in the method of manufacturing a tissue repair material described below. Generally, the residual ratio in the presence of acid tends to be lower when the processing time of the crosslinking process is shorter.

Other Components

In addition to the gelatin granules, the tissue repair material may include other components that can contribute to repair or regeneration of a tissue. Examples of such other components include components related to bone regeneration or osteoneogenesis such as osteoinductive agents. Examples of osteoinductive agents include, but are not limited to, bone morphogenetic proteins (BMP) and basic fibroblast growth factor (bFGF).

Method of Manufacturing Tissue Repair Material

As long as the tissue repair material includes gelatin granules and exhibits the specified water absorptivity and residual ratio in the presence of acid mentioned above, the method employed for manufacturing the same is not particularly limited. The tissue repair material can be obtained, for example, by the following method.

A method of manufacturing a tissue repair material includes:

(a) preparing a gelatin solution that includes gelatin dissolved in an aqueous medium (referred to as a gelatin solution preparation process hereafter);

(b) obtaining a freeze-dried product by freeze-drying the gelatin solution (referred to as a freeze-drying process hereafter);

(c) obtaining a pulverized product by pulverizing the freeze-dried product of gelatin (referred to as a pulverization process hereafter); and (d) obtaining a substrate by crosslinking the pulverized product (referred to as a crosslinking process hereafter).

The aqueous medium in the gelatin solution prepared in the gelatin solution preparation process is not particularly limited as long as the aqueous medium can dissolve gelatin and is usable with respect to a biological tissue. Examples of the aqueous medium include solutions commonly employable in this field, such as water, physiological saline, and phosphate buffer solutions.

The content of gelatin in the gelatin solution is not particularly limited as long as the gelatin is soluble at that content. For example, the gelatin content in the gelatin solution is preferably from 0.5% by mass to 20% by mass, is more preferably from 2% by mass to 16% by mass, and is still more preferably from 4% by mass to 12% by mass. There is a tendency for strength to increase when the content is 0.5% by mass or more, and a mesh structure having high uniformity tends to be more easily formed and tissue regeneration ability tends to be excellent when the content is 20% by mass or less.

In the process of preparing the gelatin solution, gelatin is prepared as a raw material, and preparation is performed by dissolving the gelatin in the aqueous medium. The gelatin as a raw material may be in a powdered form, or may be in a solid form. The gelatin solution may be a pre-prepared gelatin solution.

The temperature employed when preparing the gelatin solution is not particularly limited, and may be an ordinarily used temperature, for example, from 0° C. to 60° C., and is preferably from approximately 3° C. to approximately 30° C.

If necessary, the gelatin solution may include components required in the processes described below, such as a crosslinking agent, and components useful for imparting specified characteristics to the tissue repair material.

When it is desired to obtain gelatin granules having spaces, it is preferable to provide a process, prior to the freeze-drying process, in which the gelatin solution is cooled to a temperature that is equal to or lower than the ice crystal formation temperature.

When this process is provided, a gelatin-containing intermediate product that contains ice crystals of appropriate size therein can be obtained. The formation of ice crystals cause non-uniformity with respect to the denseness of the peptide chains of the gelatin when the gelatin-containing intermediate product is solidified, and, therefore, spaces are formed in the mesh of the gelatin-containing intermediate product after elimination of the ice crystals. The elimination of ice crystals is easily performed by the drying process to be performed later. The pore size of the mesh of the gelatin-containing intermediate product can be regulated by the ice crystal temperature, cooling time, or a combination thereof.

The ice crystal formation temperature refers to a temperature at which at least a portion of the gelatin solution freezes. Although the ice crystal formation temperature varies depending on the concentration of solids, including gelatin, in the gelatin solution, the ice crystal formation temperature may generally be set to be −10° C. or lower. The gelatin solution is preferably cooled to a temperature of from −100° C. to −10° C., more preferably from −80° C. to −20° C., and more preferably from −40° C. to −60° C. When the ice crystal formation temperature is −100° C. or higher, the mesh size tends to be sufficiently large, and when the ice crystal formation temperature is −10° C. or lower, the uniformity of pore sizes of the mesh in the gelatin-containing intermediate product tends to be high, and it tends to be possible for high ability to regenerate bone to be exhibited.

From the viewpoint of facilitating uniform ice crystal formation, the time for holding the gelatin solution at a temperature equal to or lower than the ice crystal formation temperature is preferably from 1 hour to 6 hours.

The gelatin-containing intermediate product having a mesh structure can be obtained by performing treatment at the ice crystal formation temperature. The term "mesh structure" in the present specification refers to a structure that includes many internal spaces, and is not limited to planar structures. Moreover, the scope of the mesh structure includes structures in which the framework is wall-shaped, as well as structures in which the framework is fibrous. Moreover, the scope of the mesh structure refers to the structure of the framework formed of a gelatin-containing material, but does not encompass molecular level structures such as collagen fibers.

"Have a mesh structure" denotes that spaces on the order of microns or greater are formed due to a wall-shaped structure formed by a gelatin-containing material, namely, that the structure has a hole diameter of 1 μm or more.

Although not particularly limited, the shape of the mesh in the gelatin-containing intermediate product may be a two dimensional structure such as a honeycomb, or may be three dimensional structure similar to that of cancellous bone. The cross-section shape of the mesh may be polygonal, circular, or elliptical. The three dimensional shape of the mesh in the gelatin-containing intermediate product may be a pillar shape or globular.

Communicating holes formed by continuous spaces may be present in the gelatin-containing intermediate product. When the communication holes are present, continuous spaces extending from the outside of the gelatin-containing intermediate product to deep inside the gelatin-containing intermediate product are formed. When such connections between holes are present, cells can disperse or diffuse to the inside of the porous material when the cells contact with the outside of the tissue repair material formed from the gelatin-containing intermediate product. The communicating holes preferably have a hole diameter of 10 μm or more so that such functionality is exhibited.

The hole diameter of the mesh of the gelatin-containing intermediate product is evaluated as the average diameter along the major axis direction (major axis diameter). The average major axis diameter is evaluated as follows.

First, a dried intermediate product obtained after the gelatin-containing intermediate product has been dried is cut along the horizontal and vertical directions. Next, each cross-sectional face is stained by being placed in close contact with a staining pad, and a 2.0 mm×2.0 mm region thereof is examined using an optical microscope. From among rectangles that circumscribe an area in the observed region surrounded by the stained material (one mesh opening), the circumscribing rectangle of which the distance between two opposing sides of the rectangle is largest is selected. 50 measurements are made in the observed area in each of the horizontal direction cross-section and the vertical direction cross-section, with respect to the length of the long side of the circumscribing rectangle of which the distance between two opposing sides is largest, and the average value thereof is taken as the average value of the major axis diameter of the mesh of the gelatin-containing intermediate product.

The average value of the major axis diameter on the horizontal direction cross-section and the average value of the major axis diameter on the vertical direction cross-section are obtained from the measurements of individual mesh openings, and the smallest value thereof is denoted d1 and the other value is denoted d2, and the ratio of d2/d1 is called the mesh aspect ratio. A mesh aspect ratio of from 1 to 3 represents "globular", and a mesh aspect ratio outside this range represents "pillar shaped".

When the shape of the mesh is a pillar shaped (when the mesh aspect ratio is outside the range of from 1 to 3), the mesh aspect ratio is preferably 4 or 5 from the viewpoint of bone adhesion. Bone adhesion tends to increase when the mesh aspect ratio is 5 or less.

The shape of the mesh is preferably globular (a mesh aspect ratio of from 1 to 3) from the viewpoint of tissue repair ability.

When the shape of the mesh is pillar shaped, the hole diameter of the mesh in the gelatin-containing intermediate product is preferably 10 μm or more, is more preferably 50 μm or more, and is still more preferably 100 μm or more, from the viewpoint of bone adhesion. Although not particularly limited, the upper limit of the hole diameter in the mesh of the gelatin-containing intermediate product is preferably 2500 μm or less, and is more preferably 1000 μm or less, from the viewpoint of stabilization of material strength.

Cells tend to easily invade into the inside of the mesh structure when the diameter along the major axis direction is 10 μm or more, and affinity to biological bodies tends to high when the diameter along the major axis direction is 2500 μm or less.

When the mesh has a globular shape, the hole diameter in the mesh of the gelatin-containing intermediate product is preferably 10 μm or more, is more preferably 50 μm or more, and is still more preferably 100 μm or more, from the viewpoint of bone adhesion. Although not particularly limited, the upper limit of the hole diameter in the mesh in the gelatin-containing intermediate product is generally preferably 2500 μm or less, and, from the viewpoint of bone adhesion, the upper limit of the hole diameter in the mesh in the gelatin-containing intermediate product is preferably 1000 m or less. When the mesh shape is globular, cells tend to easily invade into inside the mesh structure when the hole diameter of the mesh (the diameter along the major axis direction when the aspect ratio is more than 1) is 10 μm or more, and affinity to biological bodies tends to be high when the hole diameter of the mesh is 2500 μm or less.

The void ratio in the gelatin-containing intermediate product is preferably from 80% to 99.99%, and is more preferably from 95.01% to 99.9%. The void ratio is obtained as a void ratio ($P=(1-\rho/\rho c)\times100(\%)$) from a bulk density ($\rho$) and a true density ($\rho c$). The bulk density ($\rho$) is computed from the dry mass and volume, and the true density ($\rho c$) is obtained according to the pycnometer method using a Guy-Lus sac-type pycnometer.

In the freeze-drying process, a freeze-dried product is obtained by freeze-drying the gelatin solution. When ice crystal formation processing is performed on the gelatin solution, the gelatin-containing intermediate product may be subjected to freeze-drying as is.

Conditions ordinarily employed in freeze-drying of proteins may be applied as is for the freezing conditions. The duration of the freeze-drying may be, for example, from 0.5 hours to 300 hours. There are no particular limitations to freeze-drying apparatuses that may employed.

In the pulverization process, a pulverized product is obtained by pulverizing the freeze-dried product of gelatin. The obtained pulverized product may be included as gelatin granules in the tissue repair material. In the pulverization, a pulverizing machine such as a hammermill or a screen mill may be used, and a screen mill (for example, a COMIL manufactured by Quadro Engineering Corp.) is preferable, considering that the use of a screen mill provides small particle size variations between assays because pulverized products that have been pulverized to a given size are collected. In order to maintain the structure of the surface of the pulverized product, a cutting method is more preferable than a crashing method for the pulverization conditions. In order to maintain the internal structure of the granules, a method that does not apply strong compression during pulverization is preferable.

A classification process may be included after the pulverization process, so as to regulate granule sizes. When the classification process is included, a gelatin pulverized product having uniform particle diameters can be obtained. In the classification, a sieve having openings of, for example, from 300 μm to 710 μm is preferably used.

A crosslinking process in which gelatin in the obtained pulverized product is crosslinked is preferably included after the pulverization process. A known method may be used for crosslinking, such as thermal crosslinking, crosslinking by enzymes, crosslinking employing various chemical crosslinking agents, or UV crosslinking. Crosslinking using a chemical crosslinking agent, or thermal crosslinking, is preferable as the method for crosslinking. A product with a higher order structure due to at least one of hydrophobic interaction, hydrogen bonding, or ionic interactions is preferable in addition to crosslinks (covalent bonds).

When crosslinking is performed using an enzyme, the enzyme is not particularly limited as long as the enzyme causes crosslinking between biodegradable materials. Crosslinking is preferably performed using transglutaminase or laccase, most preferably transglutaminase.

In the invention, the mixing temperature when gelatin is treated with a crosslinking agent such as an aldehyde or a condensation agent is not particularly limited as long as the solution can be uniformly agitated, and the temperature is preferably from 0° C. to 40° C., more preferably from 0° C. to 30° C., more preferably from 3° C. to 25° C., more preferably from 3° C. to 15° C., more preferably from 3° C. to 10° C., and particularly preferably from 3° C. to 7° C.

The temperature may be increased after mixing the crosslinking agent in and agitating. Although the reaction temperature is not particularly limited as long as the crosslinking proceeds, in consideration of denaturation or decomposition of gelatin, the reaction temperature may be from 0° C. to 60° C. in practice, is more preferably from 0° C. to 40° C., is more preferably from 3° C. to 25° C., is more preferably from 3° C. to 15° C., is still more preferably from 3° C. to 10° C., and is particularly preferably from 3° C. to 7° C.

In the case of a crosslinking method using a chemical crosslinking agent, crosslinking is more preferably performed using glutaraldehyde as a chemical crosslinking agent. In the case of adopting a crosslinking method using a chemical crosslinking agent, crosslinking may be performed prior to the drying process, by adding the chemical crosslinking agent to the gelatin solution.

The crosslinking temperature applied in the thermal crosslinking method is preferably from 100° C. to 200° C., is more preferably from 120° C. to 170° C., and is still more preferably from 130° C. to 160° C. The use of crosslinking agents can be avoided by applying the thermal crosslinking method.

The treatment duration of the thermal crosslinking varies depending on the crosslinking temperature, the type of gelatin, and the desired degree of decomposability. For example, thermal crosslinking conditions when CBE3 is employed as human derived recombinant gelatin, as in examples described later, are as follows. When the actual temperature is approximately 136° C., the treatment duration is preferably from 2 hours to 20 hours, more preferably from 3 hours to 18 hours, and still more preferably from 5 hours to 8 hours. The process of thermal crosslinking is preferably performed under reduced under pressure, a vacuum, or in an inert gas atmosphere from the perspective of preventing oxidation. The pressure is preferably reduced to 4 hPa or less. Nitrogen is preferable as the inert gas, and crosslinking under an inert gas atmosphere is more preferable than under a vacuum from the viewpoint of uniform heating. The heating means is not particularly limited, and examples thereof include a vacuum oven such as a DP-43 manufactured by Yamato Scientific Co., Ltd.

The tissue repair material may include gelatin granules obtained by the manufacturing method described alone, or may be obtained by compounding other components with the gelatin granules.

From the viewpoint of high ability to regenerate a tissue, for example, high ability to regenerate bone, the method of manufacturing a tissue repair material preferably includes obtaining a freeze-dried product of gelatin by performing freeze-drying treatment after cooling the gelatin solution that includes gelatin at from 7% by mass to 9% by mass to a temperature of from −40° C. to −60° C. over from 1 hours to 6 hours, obtaining a pulverized product by pulverizing the freeze-dried product, and thermally crosslinking the pulverized product at from 140° C. to 160° C. under a nitrogen atmosphere for from 3 hours to 7 hours in the case of the later-described CBE3, which is human derived recombinant gelatin, or thermally crosslinking the pulverized product at from 140° C. to 160° C. under a nitrogen atmosphere for from 24 hours to 72 hours in the case of pig gelatin.

Therapeutic Method and Repair Method

The invention can provide a tissue repair material with high ability to regenerate a tissue. Therefore, the scope of the invention includes a method of repairing a tissue, and a method of treating a disease or the like accompanied by tissue damage.

Specifically, a method of repairing a tissue according to the invention include applying the tissue repair material to a site at which a target tissue is defective or damaged, and include other processes if necessary.

The tissue that the tissue repair material according to the invention is able to repair is preferably a hard tissue such as a tooth or a bone. In particular, the tissue repair material is well suited as a substrate for bone regeneration. The tissue repair material according to the invention may be employed as a therapeutic agent for use on its own in bone regeneration. The disease to which this therapeutic agent is applied is not particularly limited as long the disease requires bone regeneration or osteoneogenesis for treatment.

The method of treating a damaged tissue or the method of repairing a damaged tissue according to the invention includes applying the tissue repair material to a site where target tissue is defective or damaged, and includes other processes if necessary. Examples of other processes include applying a cell for transplantation and/or an osteoinductive agent to a tissue repair material application site, either before, after, or simultaneously with application of the tissue repair material.

The method of treating or the method of repairing can preferably be applied to periodontal defects, implant defects, and the like in the maxillofacial region, GBR methods, ridge augmentation methods, sinus lift methods, and socket reservation methods, which are employed as supplemental treatments during implant placement, and the like.

Block-shaped Tissue Repair Material

The block-shaped tissue repair material according to the invention includes gelatin, and is a tissue repair material that exhibits a water absorptivity of 800% by mass or more, and a residual ratio of 60% by mass or less after three hours of decomposition treatment using 1 mol/L hydrochloric acid. Among tissues, excellent regeneration of dermis in particular is enabled by this tissue repair material.

Accordingly, the block-shaped tissue repair material according to the invention is preferably applied to dermis regeneration.

Preferable features, numerical ranges, and the like for each component in the block-shaped tissue repair material are the same as those in the tissue repair material including gelatin granules.

The block-shaped tissue repair material may be manufactured in the same manner as in the method of manufacturing a tissue repair material including gelatin granules, except that the pulverization process is not performed.

Detailed description follows regarding examples of the invention; however, the invention is not limited in any way by these examples.

Example 1

A substrate for bone regeneration of Example 1 was manufactured using recombinant peptide CBE3 as a recombinant gelatin.

The following was employed as CBE3 (as described in WO2008/103041A1).

CBE3

Molecular weight: 51.6 kD

Structure: GAP [(GXY)$_{63}$]$_3$G (SEQ ID NO: 2)

Number of amino acid residues: 571 units

RGD sequence: 12 units

Imino acid content: 33%

Approximately 100% of the amino acids participate in the GXY repeating structures.

Serine residues, threonine residues, asparagine residues, tyrosine residues, and cysteine residues are not included in the amino acid sequence of the CBE3.

The CBE3 includes an ERGD sequence.

Isoelectric point: 9.34

```
Amino acid sequence
                                            (SEQ ID NO: 1)
GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)3G
```

Explanation of Vessel Used During Freezing

An aluminum vessel in the shape of a cylindrical cup was prepared with a thickness of 1 mm and a diameter of 47 mm. When the curved face of the cylindrical cup is taken as the side face, the side face is formed by 1 mm aluminum, and the bottom face (a flat circular plate) is also formed by 1 mm aluminum. However, the top face is left open. Only the side face at the inner side is uniformly coated with TEFLON (registered trademark) with a thickness of 1 mm, as a result of which the inner diameter of the cylindrical cup is 45 mm. This vessel is referred to as a cylindrical vessel hereafter.

Approximately 4 ml of a gelatin aqueous solution that included recombinant gelatin at 8% by mass was poured into the cylindrical vessel, and allowed to stand in a freezer (an ultra-low temperature freezer RS-U30T manufactured by Hitachi Ltd.) at −50° C. for 1 hour or more, whereby a frozen gelatin block was obtained. This gelatin block was freeze-dried (using a TF5-85ATNNN manufactured by Takara Bio Inc.), pulverized using a pulverizer (a COMIL U5 manufactured by Quadro Engineering Corp.), and then a fraction thereof that passed through a sieve having openings of 710 μm, but did not pass through a sieve having openings of 500 μm, was collected. These obtained gelatin granules were treated for 3.5 hours at 130° C. under a nitrogen atmosphere (using a DP-43 manufactured by Yamato Scientific Co., Ltd.), thereby obtaining Sample 1.

The water absorptivity, residual ratio in the presence of acid, and bone regeneration ratio of Sample 1 were evaluated as follows.

(1) Water Absorptivity

The following assay was performed at 25° C. in a relative humidity of 30%. The mass (A) was measured of a 3 cm×3 cm mesh bag for measuring made from nylon and having a thickness of 106 μm, the mesh bag being formed from a mesh having 150 strands per 2.54 cm, a strand diameter of 6 μm, an opening equivalent to 108 μm, and an opening area of 41%, and this mesh bag being hereinafter referred to as "mesh bag". Sample 1 was weighed out at 15.0 (±1.0) mg (B), and placed in the mesh bag for measuring. An empty mesh bag for measuring to which the Sample 1 was not inserted was used as a blank mesh bag, and the mass thereof (C) was measured. Clips were placed on the upper faces of both of the mesh bags, and the mesh bags were suspended in 100 ml beakers containing 80 ml of ultrapure water. Both mesh bags were retained in the position at which all of the Sample 1 in the mesh bag would be soaked in water, and were left for two hours or longer. Then, after two or more hours had elapsed, the water in the beakers was discarded, and both mesh bags were taken out and hung at the same angle of inclination, and left to stand for 10 minutes to drain excess water. Then, the mass (D) of the blank mesh bag and the mass (E) of the mesh bag containing the Sample 1 were measured, and the water absorptivity was calculated using Equation (1) and Equation (2) below. There results are indicated in Table 1.

$$\text{Blank water absorptivity } (F) = D/C \quad (1)$$

$$\text{Water absorptivity} = (E - A \times F)/B \times 100(\%) \quad (2)$$

(2) Residual Ratio in the Presence of Acid

The following assay was performed at 25° C. with a relative humidity of 30%. The mass (A) of a microtube for measuring (referred to as a tube hereafter) was measured. 5.0 (±0.2) mg (B) of Sample 1 was weighed out and loaded into the tube for measuring. 1.0 ml of HCl at 1 mol/L concentration was then added to the tube containing Sample 1, and shaken in a thermostatic shaker (a HB-80 manufactured by Taitec Corporation, with a see-saw movement at 60 reciprocal movements per minute) at 37° C. for three hours. After the stipulated time, the tube was stood on ice to stop reactions, and then centrifuged at 10,000×g for one minute in a centrifuge pre-set to 4° C. Precipitation of Sample 1 was confirmed, the supernatant was removed by suction, 1 ml of ultrapure water that had been pre-cooled on ice was added thereto, and centrifuging was performed again under the same conditions as those described above. The supernatant was removed by suction, ultrapure water was again added thereto, and centrifuging was performed again under the same conditions as those described above. The supernatant was then removed by suction, and freeze drying was performed. The cap of the tube was quickly closed after the tube was taken out from the freeze-drying apparatus, in order to prevent the Sample 1 from absorbing moisture in the air. The mass (C) of the tube, including the content therein, was measured, and the residual ratio in the presence of acid was computed using calculation Equation (3) below. The results are listed in Table 1.

$$\text{Residual ratio in the presence of acid} = (C - A)/B \times 100(\%) \quad (3)$$

(3) Bone Regeneration Evaluation

A circular shaped bone loss area with a diameter of 5 mm was produced in the parietal bone of an SD rat (male, from 10 to 12 weeks old, from 0.3 to 0.5 kg), approximately 3.6 mg of Sample 1 was filled into the produced bone loss area, and then suturing was performed. The amount of bone in the rat's parietal bone was measured using a microCT at two weeks and four weeks after the operation. The ratio of the volume of bone in the bone loss area to the volume of the loss area was taken as the bone regeneration ratio. The results are listed in Table 1.

Example 2

Approximately 4 ml of a gelatin aqueous solution that included the recombinant gelatin described in Example 1 at 7.5% by mass was poured into the cylindrical vessel, and allowed to stand in a freezer (an ultra-low temperature freezer RS-U30T manufactured by Hitachi Ltd.) at −40° C. for 1 hour or more, whereby a frozen gelatin block was obtained. This gelatin block was freeze-dried (using a TF5-85ATNNN manufactured by Takara Bio Inc.), pulverized using a pulverizer (a COMIL U5 manufactured by Quadro Engineering Corp.), and then a fraction thereof that passed through a sieve having openings of 1400 μm, but did not pass through a sieve having openings of 300 μm, was collected. The collected fraction was treated at 130° C. for 6 hours under a nitrogen atmosphere (using a DP-43 manufactured by Yamato Scientific Co., Ltd.), thereby obtaining Sample 2.

The water absorptivity, residual ratio in the presence of acid, and bone regeneration ratio of Sample 2 were evaluated in the same manner as that in Example 1. The results are listed in Table 1.

Example 3

Approximately 4 ml of a gelatin aqueous solution that included the recombinant gelatin described in Example 1 at 8% by mass was poured into the cylindrical vessel, and allowed to stand in a freezer (an ultra-low temperature freezer RS-U30T manufactured by Hitachi Ltd.) at −50° C. for 1 hour or more, whereby a frozen gelatin block was obtained. This gelatin block was freeze-dried (using a TF5-85ATNNN manufactured by Takara Bio Inc.), pulverized using a pulverizer (a COMIL U5 manufactured by Quadro Engineering Corp.), and then a fraction thereof that passed through a sieve having openings of 710 μm, but did not pass through a sieve having openings of 500 μm, was collected. The collected fraction was treated at 130° C. for 7 hours under a nitrogen atmosphere (using a DP-43 manufactured by Yamato Scientific Co., Ltd.), thereby obtaining Sample 3.

The water absorptivity, residual ratio in the presence of acid, and bone regeneration ratio of Sample 3 were evaluated in the same manner as that in Example 1. The results are listed in Table 1.

Example 4

Approximately 4 ml of a gelatin aqueous solution that included pig gelatin (Nippi High Grade Gelatin® APAT manufactured by Nippi Inc.) at 7.5% by mass was poured into the cylindrical vessel, and allowed to stand in a freezer (an ultra-low temperature freezer RS-U30T manufactured by Hitachi Ltd.) at −40° C. for 1 hour or more, whereby a frozen gelatin block was obtained. This gelatin block was freeze-dried (using a TF5-85ATNNN manufactured by Takara Bio Inc.), pulverized using a pulverizer (a COMIL U5 manufactured by Quadro Engineering Corp.), and then a fraction thereof that passed through a sieve having openings of 710 μm, but did not pass through a sieve having openings of 500 μm, was collected. These obtained gelatin granules were treated at 130° C. for 72 hours under a nitrogen atmosphere (using a DP-43 manufactured by Yamato Scientific Co., Ltd.), thereby obtaining Sample 4.

The water absorptivity, residual ratio in the presence of acid, and bone regeneration ratio of Sample 4 were evaluated in the same manner as that in Example 1. The results are listed in Table 1.

Comparative Example 1

Approximately 4 ml of a gelatin solution that included the recombinant gelatin described in Example 1 at 7.5% by mass was poured into the cylindrical vessel, and allowed to stand in a freezer (an ultra-low temperature freezer RS-U30T manufactured by Hitachi Ltd.) at −40° C. for 1 hour or more, whereby a frozen gelatin block was obtained. This gelatin block was freeze-dried (using a TF5-85ATNNN manufactured by Takara Bio Inc.), and then treated at a temperature of 142° C. and a pressure of 4 hPa or lower for 5 hours (using a DP-43 manufactured by Yamato Scientific Co., Ltd.), thereby obtaining Sample 5.

Sample 5 was shaped into specified shapes for respective assays (see below), and the water absorptivity, residual ratio in the presence of acid, and bone regeneration ratio were evaluated in the same manner as that in Example 1, using the assay samples obtained. The results are listed in Table 1.

Water absorptivity: an approximately 1.5 mm×approximately 2 mm×approximately 12 mm rectangular parallelepiped Decomposability: an approximately 6 mm (diameter)× approximately 1 mm (thickness) solid cylinder Bone regeneration ratio: an approximately 5 mm (diameter)×approximately 1 mm (thickness) solid cylinder

Comparative Example 2

Approximately 4 ml of a gelatin aqueous solution that included pig gelatin (Nippi High Grade Gelatin® APAT manufactured by Nippi Inc.) at 7.5% by mass was poured into the cylindrical vessel, and allowed to stand in a freezer (an ultra-low temperature freezer RS-U30T manufactured by Hitachi Ltd.) at −40° C. for 1 hour or more, whereby a frozen gelatin block was obtained. This gelatin block was freeze-dried (using a TF5-85ATNNN manufactured by Takara Bio Inc.), then treated at a temperature of 142° C. and a pressure of 4 hPa or less for 33 hours (using a DP-43 manufactured by Yamato Scientific Co., Ltd.), thereby obtaining Sample 6.

Sample 6 was shaped into specified shapes for respective assays (see below), and the water absorptivity, residual ratio in the presence of acid, and bone regeneration ratio were evaluated in the same manner as that in Example 1, using the assay samples obtained. The results are listed in Table 1.

Water absorptivity: an approximately 1.5 mm×approximately 2 mm×approximately 12 mm rectangular parallelepiped Decomposability: an approximately 6 mm (diameter)× approximately 1 mm (thickness) solid cylinder Bone regeneration ratio: an approximately 5 mm (diameter)×approximately 1 mm (thickness) solid cylinder

Comparative Example 3

Approximately 4 ml of a gelatin aqueous solution that included the recombinant gelatin described in Example 1 at 8% by mass was poured into the cylindrical vessel, and allowed to stand in a freezer (an ultra-low temperature freezer RS-U30T manufactured by Hitachi Ltd.) at −50° C. for 1 hour or more, whereby a frozen gelatin block was obtained. This gelatin block was freeze-dried (using a TF5-85ATNNN manufactured by Takara Bio Inc.), pulverized using a pulverizer (a COMIL U5 manufactured by Quadro Engineering Corp.), and then a fraction thereof that passed through a sieve having openings of 710 μm, but did not pass through a sieve having openings of 500 μm, was collected. The collected fraction was treated at 130° C. for 18 hours under a nitrogen atmosphere (using a DP-43 manufactured by Yamato Scientific Co., Ltd.), thereby obtaining Sample 7.

The water absorptivity, residual ratio in the presence of acid, and bone regeneration ratio of Sample 7 were evaluated in the same manner as that in Example 1. The results are listed in Table 1.

Comparative Example 4

Approximately 4 ml of a gelatin aqueous solution that included the recombinant gelatin described in Example 1 at 8% by mass was poured into the cylindrical vessel, and allowed to stand in a freezer (an ultra-low temperature freezer RS-U30T manufactured by Hitachi Ltd.) at −50° C. for 1 hour or more, whereby a frozen gelatin block was obtained. This gelatin block was freeze-dried (using a TF5-85ATNNN manufactured by Takara Bio Inc.), pulverized using a pulverizer (a COMIL U5 manufactured by Quadro Engineering Corp.), and then a fraction thereof that passed through a sieve having openings of 710 μm, but did not pass through a sieve having openings of 500 μm, was collected. The collected fraction was treated at 130° C. for 15 hours under a nitrogen atmosphere (using a DP-43 manufactured by Yamato Scientific Co., Ltd.), thereby obtaining Sample 8.

The water absorptivity, residual ratio in the presence of acid, and bone regeneration ratio of Sample 8 were evaluated in the same manner as that in Example 1. The results are listed in Table 1.

Comparative Example 5

In a pot cooled to 9° C., a gelatin aqueous solution that included pig gelatin (Nippi High Grade Gelatin® APAT manufactured by Nippi Inc.) at 12% by mass was agitated at 1400 rpm using a T. K. HOMO DISPER model 2.5, and allowed to stand in a freezer at −50° C. for 8 hours, whereby a frozen gelatin block was obtained. The conditions of the agitating corresponded to an agitating Froude number Fr of 2.22, and an agitating Reynolds number of 3,700. The gelatin block was freeze-dried, and pulverized using a pulverizer (a New Power Mill PM-2005 manufactured by Osaka Chemical Co. Ltd). A fraction thereof that passed through a sieve having openings of 710 μm, but did not pass through a sieve having openings of 500 μm, was collected, and treated at a temperature of 160° C. and a pressure of 4 hPa or less for 19 hours (using a DP-43 manufactured by Yamato Scientific Co., Ltd.) to give Sample 9.

The water absorptivity, residual ratio in the presence of acid, and bone regeneration ratio of Sample 9 were evaluated in the same manner as that in Example 1. The results are listed in Table 1.

Comparative Example 6

Approximately 20 ml of a gelatin aqueous solution that included the recombinant gelatin described in Example 1 at 7.5% by mass was poured into the cylindrical vessel, left to stand at −2° C., and then cooled −30° C. After the formation of ice nuclei was confirmed, the temperature was raised to −4.5° C. Then, cooling at a rate of 0.3° C. per minute was performed, whereby a frozen gelatin block was obtained. This gelatin block was freeze-dried, and pulverized using a pulverizer (a New Power Mill PM-2005 manufactured by Osaka Chemical Co. Ltd). Then, a fraction thereof that passed through a sieve having openings of 710 μm, but did not pass through a sieve having openings of 500 μm, was collected, and treated at a temperature of 142° C. and a pressure of 4 hPa or less for 3.5 hours (a DP-43 manufactured by Yamato Scientific Co., Ltd.), thereby obtaining Sample 10.

The water absorptivity, residual ratio in the presence of acid, and bone regeneration ratio of Sample 10 were evaluated in the same manner as that in Example 1. The results are listed in Table 1.

Comparative Example 7

Approximately 20 ml of a gelatin aqueous solution that included the recombinant gelatin described in Example 1 at 7.5% by mass was poured into the cylindrical vessel, left to stand at −2° C., then cooled −30° C. After the formation of ice nuclei was confirmed, the temperature was raised to −6° C. Then, cooling at a rate of 0.5° C. per minute was performed, whereby a frozen gelatin block was obtained. This gelatin block was freeze-dried, and pulverized using a pulverizer (a COMIL U5 manufactured by Quadro Engineering Corp.). Then, a fraction thereof that passed through a sieve having openings of 710 μm, but did not pass through a sieve having openings of 500 μm, was collected, and treated at 130° C. for 18 hours under a nitrogen atmosphere (using a DP-43 manufactured by Yamato Scientific Co., Ltd.), thereby obtaining Sample 11.

The water absorptivity, residual ratio in the presence of acid, and bone regeneration ratio of Sample 11 were evaluated in the same manner as that in Example 1. The results are listed in Table 1.

TABLE 1

| | | Residual Ratio in the Presence of Acid | | |
|---|---|---|---|---|
| | | ≤60% | | >60% |
| Water Absorptivity | ≥800% | Example 1 (1775%, 8%) 2 weeks 24% 4 weeks 51% | Example 3 (1463%, 59%) 2 weeks 28% 4 weeks 59% | Comparative Example 3 (1516%, 84%) 2 weeks 14% 4 weeks 28% |

TABLE 1-continued

| | Residual Ratio in the Presence of Acid | | |
|---|---|---|---|
| | ≤60% | | >60% |
| | Example 2 (2579%, 30%) 2 weeks 17% 4 weeks 48% | Example 4 (1208%, 54%) 2 weeks 18% 4 weeks 51% | Comparative Example 4 (931%, 84%) 2 weeks 17% 4 weeks 33% Comparative Example 5 (1451%, 90%) 2 weeks 19% 4 weeks 40% |
| <800% | Comparative Example 1 (1169%, 60%) 2 weeks 12% 4 weeks 19% Comparative Example 6 (785%, 47%) 2 weeks 10% 4 weeks 23% | Comparative Example 2 (2945%, 55%) 2 weeks 13% 4 weeks 21% | Comparative Example 7 (847%, 68%) 2 weeks 9% 4 weeks 21% |

Example No.
(water absorptivity, residual ratio in the presence of acid)
bone regeneration ratio (weeks)

In Table 1, tissue repair materials of Samples 1 to 4, which included gelatin granules and exhibited a water absorptivity of 800% by mass or more and a residual ratio of 60% by mass or less in the presence of acid, exhibited high ability to regenerate bone, and in particular, their bone regeneration ratios exceeded 45% after 4 weeks. The bone regeneration performances for Samples 7 to 11, which either do not have a water absorptivity of 800% by mass or more, or have a residual ratio of more than 60% by mass in the presence of acid, were all inferior to those of Samples 1 to 4.

The residual ratio in the presence of acid of Sample 1, Sample 3, and Sample 7 were 8% for Sample 1, 59% for Sample 3, and 84% for Sample 7 (see Table 1). These results demonstrate that shortening the crosslinking duration results in higher acid decomposability and lower residual ratio in the presence of acid. This demonstrates that the crosslinking time contributes to the regulation of the acid decomposability of the tissue repair material.

The water absorptivities and residual ratios in the presence of acid of granular Samples 3 and 4, and block-shaped Samples 5 and 6, demonstrate that the bone regeneration ratio varies with the form of the tissue repair material, even when the water absorptivities and residual ratios in the presence of acid are similar (see Table 1).

It is conceivable that these results are produced because: for example, when strength require for maintaining spaces in the loss area is imparted by regulating the crosslinking duration, use of a block-shaped substrate makes it necessary for cells to decompose the substrate in order to proliferate, makes it difficult for cells to reach the interior of the loss area; in contrast, use of a granular substrate makes it easy for cells to reach the interior of the loss area by passing between granules, and thereby enables bone regeneration to proceed smoothly. This demonstrates that granularity of the substrate contributes to the control for providing an excellent bone regeneration ratio of a substrate for bone regeneration, and for maintaining the volume of the loss area.

Example 5

Sample Preparation

A 3% recombinant gelatin aqueous solution was prepared using the recombinant gelatin described in Example 1, and the aqueous solution was poured into the cylindrical vessel. Thereafter, the cylindrical vessel was allowed to stand in a freezer at −80° C. for one hour. Then, the aqueous solution was freeze-dried, and thermally crosslinked at a temperature of 160° C. and a pressure of 4 hPa or less for three hours, whereby a gelatin block having a water absorptivity of 2600% and a residual ratio of 50% in the presence of acid was obtained.

Dermal-Like Tissue (Granulation-Like Tissue) Assay in a Rat's Back

A Wistar rat (male, at least 10 weeks old) was anesthetized by administering 90 mg/kg of ketamine hydrochloride and 10 mg/kg of xylazine hydrochloride, to the abdominal cavity. A circular area of dermis loss of 19 mm diameter was produced after shaving the rat's back. The above gelatin block, having a 19 mm diameter and approximately 1.5 mm thickness, was affixed to the area of dermis loss, and a Vaseline coated gauze (ADAPTIC (registered trademark) manufactured by Johnson & Johnson), wet cotton, and a gauze were applied and fixed in place. In the second week after fixing, tissue of the back was removed along with the wound dressing under anesthetic.

The removed tissue was HE stained and histologically observed, as a result of which formation of a dermis-like tissue (granulation-like tissue) was observed.

This demonstrates that the sample is particularly well suited to the regeneration of dermis.

As demonstrated in the above, the tissue repair materials according to the examples of the invention were substrates for tissue regeneration that exhibits excellent bone regeneration performance.

Thus, according to the invention, a tissue repair material having an excellent tissue regeneration ability can be provided.

The disclosure of Japanese Patent Application No. 2013-049339, filed Mar. 12, 2013, is incorporated herein by reference in its entirety.

All publications, patent applications, and technical standards mentioned in the present specification are herein incorporated by reference to the same extent as if each individual publication, patent application or technical standard was specifically and individually indicated to be incorporated by reference.

The invention claimed is:

1. A tissue repair material comprising gelatin granules, wherein the tissue repair material exhibits a water absorptivity from 900% to 3000% by mass, and wherein the gelatin granules have been thermally crosslinked without using a crosslinking agent, such that when the tissue repair material is subjected to three hours of decomposition treatment using 1 mol/L hydrochloric acid, the tissue repair material after the decomposition treatment exhibits a residual ratio of 60% by mass or less, wherein the tissue repair material is manufactured by a method comprising:
   (a) preparing a gelatin solution that includes gelatin dissolved in an aqueous medium, wherein the gelatin is a recombinant gelatin;
   (b) obtaining a freeze-dried product by freeze-drying the gelatin solution;
   (c) obtaining a pulverized product by pulverizing the freeze-dried product of gelatin; and
   d) obtaining the tissue repair material in the form of a substrate by thermally crosslinking the pulverized product at from 130° C. to 145° C. under an inert gas atmosphere for 3 to 7 hours.

2. The tissue repair material according to claim 1, wherein the gelatin granules comprise a granular gelatin that passes through a sieve having openings of 1400 μm.

3. The tissue repair material according to claim 1, wherein the tissue repair material is granular.

4. The tissue repair material according to claim 1, wherein the gelatin granules have communicating holes having a hole diameter of from 10 μm to 2500 μm.

5. The tissue repair material according to claim 1, wherein the gelatin granules comprise a recombinant gelatin including no serine residues or threonine residues.

6. The tissue repair material according to claim 1, wherein the gelatin granules comprise a recombinant gelatin that includes no serine residues, threonine residues, asparagine residues, tyrosine residues, or cysteine residues.

7. The tissue repair material according to claim 1, wherein the gelatin granules comprise a recombinant gelatin that includes no amino acid sequences represented by Asp-Arg-Gly-Asp (SEQ ID NO: 12).

8. The tissue repair material according to claim 1, wherein the gelatin granules comprise a recombinant gelatin having an isoelectric point of from 5 to 10.

9. The tissue repair material according to claim 1, further comprising an osteoinductive agent.

10. A substrate for bone regeneration, comprising the tissue repair material according to claim 1.

* * * * *

```
                         SEQUENCE LISTING

<160> NUMBER OF SEQ ID NOS: 12

<210> SEQ ID NO 1
<211> LENGTH: 571
<212> TYPE: PRT
<213> ORGANISM: Artificial
<220> FEATURE:
<223> OTHER INFORMATION: CBE3

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
                20                  25                  30

Arg Gly Asp Ala Gly Pro Lys Gly Ala Asp Gly Ala Pro Gly Ala Pro
            35                  40                  45

Gly Leu Gln Gly Met Pro Gly Glu Arg Gly Ala Ala Gly Leu Pro Gly
        50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
                100                 105                 110

Asp Ala Gly Pro Lys Gly Ala Asp Gly Ala Pro Gly Lys Asp Gly Val
            115                 120                 125

Arg Gly Leu Ala Gly Pro Ile Gly Pro Pro Gly Pro Ala Gly Ala Pro
        130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
                180                 185                 190

Gly Ala Pro Gly Leu Gln Gly Ala Pro Gly Leu Gln Gly Met Pro Gly
            195                 200                 205

Glu Arg Gly Ala Ala Gly Leu Pro Gly Pro Lys Gly Glu Arg Gly Asp
        210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
                260                 265                 270

Asp Gly Val Arg Gly Leu Ala Gly Pro Ile Gly Pro Pro Gly Glu Arg
            275                 280                 285

Gly Ala Ala Gly Leu Pro Gly Pro Lys Gly Glu Arg Gly Asp Ala Gly
        290                 295                 300

Pro Lys Gly Ala Asp Gly Ala Pro Gly Lys Asp Gly Val Arg Gly Leu
305                 310                 315                 320
```

```
Ala Gly Pro Ile Gly Pro Gly Pro Ala Gly Ala Pro Gly Ala Pro
            325                 330                 335

Gly Leu Gln Gly Met Pro Gly Glu Arg Gly Ala Ala Gly Leu Pro Gly
        340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
    370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
        435                 440                 445

Asp Ala Gly Pro Lys Gly Ala Asp Gly Ala Pro Gly Lys Asp Gly Val
    450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
    530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
                565                 570
```

```
<210> SEQ ID NO 2
<211> LENGTH: 571
<212> TYPE: PRT
<213> ORGANISM: Artificial Sequence
<220> FEATURE:
<223> OTHER INFORMATION: CBE3
<220> FEATURE:
<221> NAME/KEY: MISC_FEATURE
<222> LOCATION: (1)..(571)
<223> OTHER INFORMATION: all Xaa is independently any amino acid

<400> SEQUENCE: 2

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Xaa Gly Xaa Xaa Gly Xaa Xaa Gly Xaa Xaa Gly Xaa Xaa
        35                  40                  45

Gly Xaa Xaa Gly Xaa Xaa Gly Xaa Xaa Gly Xaa Xaa Gly Xaa Xaa Gly
    50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
                85                  90                  95
```

```
Gly Xaa Xaa Gly Xaa Xaa Gly Xaa Xaa Gly Xaa Xaa Gly
        100                 105                 110

Xaa Xaa Gly Xaa Xaa Gly Xaa Xaa Gly Xaa Xaa Gly Xaa
        115                 120                 125

Xaa Gly Xaa Xaa Gly Xaa Xaa Gly Xaa Xaa Gly Xaa Xaa
        130                 135                 140

Gly Xaa Xaa Gly Xaa Xaa Gly Xaa Xaa Gly Xaa Xaa Gly
145                 150                 155                 160

Xaa Xaa Gly Xaa Xaa Gly Xaa Xaa Gly Xaa Xaa Gly Xaa
            165                 170                 175

Xaa Gly Xaa Xaa Gly Xaa Xaa Gly Xaa Xaa Gly Xaa Xaa
        180                 185                 190

Gly Xaa Xaa Gly Xaa Xaa Gly Xaa Xaa Gly Xaa Xaa Gly
            195                 200                 205

Xaa Xaa Gly Xaa Xaa Gly Xaa Xaa Gly Xaa Xaa Gly Xaa
        210                 215                 220

Xaa Gly Xaa Xaa Gly Xaa Xaa Gly Xaa Xaa Gly Xaa Xaa
225                 230                 235                 240

Gly Xaa Xaa Gly Xaa Xaa Gly Xaa Xaa Gly Xaa Xaa Gly
            245                 250                 255

Xaa Xaa Gly Xaa Xaa Gly Xaa Xaa Gly Xaa Xaa Gly Xaa
        260                 265                 270

Xaa Gly Xaa Xaa Gly Xaa Xaa Gly Xaa Xaa Gly Xaa Xaa
            275                 280                 285

Gly Xaa Xaa Gly Xaa Xaa Gly Xaa Xaa Gly Xaa Xaa Gly
    290                 295                 300

Xaa Xaa Gly Xaa Xaa Gly Xaa Xaa Gly Xaa Xaa Gly Xaa
305                 310                 315                 320

Xaa Gly Xaa Xaa Gly Xaa Xaa Gly Xaa Xaa Gly Xaa Xaa
            325                 330                 335

Gly Xaa Xaa Gly Xaa Xaa Gly Xaa Xaa Gly Xaa Xaa Gly
            340                 345                 350

Xaa Xaa Gly Xaa Xaa Gly Xaa Xaa Gly Xaa Xaa Gly Xaa
        355                 360                 365

Xaa Gly Xaa Xaa Gly Xaa Xaa Gly Xaa Xaa Gly Xaa Xaa
        370                 375                 380

Gly Xaa Xaa Gly Xaa Xaa Gly Xaa Xaa Gly Xaa Xaa Gly
385                 390                 395                 400

Xaa Xaa Gly Xaa Xaa Gly Xaa Xaa Gly Xaa Xaa Gly Xaa
            405                 410                 415

Xaa Gly Xaa Xaa Gly Xaa Xaa Gly Xaa Xaa Gly Xaa Xaa
        420                 425                 430

Gly Xaa Xaa Gly Xaa Xaa Gly Xaa Xaa Gly Xaa Xaa Gly
        435                 440                 445

Xaa Xaa Gly Xaa Xaa Gly Xaa Xaa Gly Xaa Xaa Gly Xaa
    450                 455                 460

Xaa Gly Xaa Xaa Gly Xaa Xaa Gly Xaa Xaa Gly Xaa Xaa
465                 470                 475                 480

Gly Xaa Xaa Gly Xaa Xaa Gly Xaa Xaa Gly Xaa Xaa Gly
            485                 490                 495

Xaa Xaa Gly Xaa Xaa Gly Xaa Xaa Gly Xaa Xaa Gly Xaa
        500                 505                 510
```

```
Xaa Gly Xaa Xaa Gly Xaa Xaa Gly Xaa Xaa Gly Xaa Xaa
        515                 520                 525

Gly Xaa Xaa Gly Xaa Xaa Gly Xaa Xaa Gly Xaa Xaa Gly
        530                 535                 540

Xaa Xaa Gly Xaa Xaa Gly Xaa Xaa Gly Xaa Xaa Gly Xaa
545                 550                 555                 560

Xaa Gly Xaa Xaa Gly Xaa Xaa Gly Xaa Xaa Gly
                565                 570

<210> SEQ ID NO 3
<211> LENGTH: 4
<212> TYPE: PRT
<213> ORGANISM: Artificial Sequence
<220> FEATURE:
<223> OTHER INFORMATION: CBE3

<400> SEQUENCE: 3

Arg Glu Asp Val
1

<210> SEQ ID NO 4
<211> LENGTH: 5
<212> TYPE: PRT
<213> ORGANISM: Artificial Sequence
<220> FEATURE:
<223> OTHER INFORMATION: CBE3

<400> SEQUENCE: 4

Tyr Ile Gly Ser Arg
1               5

<210> SEQ ID NO 5
<211> LENGTH: 5
<212> TYPE: PRT
<213> ORGANISM: Artificial Sequence
<220> FEATURE:
<223> OTHER INFORMATION: CBE3

<400> SEQUENCE: 5

Pro Asp Ser Gly Arg
1               5

<210> SEQ ID NO 6
<211> LENGTH: 7
<212> TYPE: PRT
<213> ORGANISM: Artificial Sequence
<220> FEATURE:
<223> OTHER INFORMATION: CBE3

<400> SEQUENCE: 6

Arg Tyr Val Val Leu Pro Arg
1               5

<210> SEQ ID NO 7
<211> LENGTH: 6
<212> TYPE: PRT
<213> ORGANISM: Artificial Sequence
<220> FEATURE:
<223> OTHER INFORMATION: CBE3

<400> SEQUENCE: 7

Leu Gly Thr Ile Pro Gly
1               5

<210> SEQ ID NO 8
```

```
<211> LENGTH: 10
<212> TYPE: PRT
<213> ORGANISM: Artificial Sequence
<220> FEATURE:
<223> OTHER INFORMATION: CBE3

<400> SEQUENCE: 8

Arg Asn Ile Ala Glu Ile Ile Lys Asp Ile
1               5                   10

<210> SEQ ID NO 9
<211> LENGTH: 5
<212> TYPE: PRT
<213> ORGANISM: Artificial Sequence
<220> FEATURE:
<223> OTHER INFORMATION: CBE3

<400> SEQUENCE: 9

Ile Lys Val Ala Val
1               5

<210> SEQ ID NO 10
<211> LENGTH: 4
<212> TYPE: PRT
<213> ORGANISM: Artificial Sequence
<220> FEATURE:
<223> OTHER INFORMATION: CBE3

<400> SEQUENCE: 10

Asp Gly Glu Ala
1

<210> SEQ ID NO 11
<211> LENGTH: 4
<212> TYPE: PRT
<213> ORGANISM: Artificial Sequence
<220> FEATURE:
<223> OTHER INFORMATION: CBE3

<400> SEQUENCE: 11

Glu Arg Gly Asp
1

<210> SEQ ID NO 12
<211> LENGTH: 4
<212> TYPE: PRT
<213> ORGANISM: Artificial Sequence
<220> FEATURE:
<223> OTHER INFORMATION: amino acid sequence

<400> SEQUENCE: 12

Asp Arg Gly Asp
1
```